(12) United States Patent
Tsuji et al.

(10) Patent No.: US 6,376,725 B1
(45) Date of Patent: Apr. 23, 2002

(54) 1,3 BUTYLENE GLYCOL OF HIGH PURITY AND METHOD FOR PRODUCING THE SAME

(75) Inventors: Yasuo Tsuji, Ohtake; Kunio Tagawa, Yamaguchi-ken, both of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/529,085

(22) PCT Filed: Aug. 6, 1999

(86) PCT No.: PCT/JP99/04275

§ 371 Date: Jul. 6, 2000

§ 102(e) Date: Jul. 6, 2000

(87) PCT Pub. No.: WO00/07969

PCT Pub. Date: Feb. 17, 2000

(30) Foreign Application Priority Data

Aug. 7, 1998 (JP) .......................................... 10-236377
Aug. 7, 1998 (JP) .......................................... 10-236378

(51) Int. Cl.$^7$ ............................. C07C 27/26; C07C 3/18
(52) U.S. Cl. ....................... 568/868; 568/852; 568/853; 568/854

(58) Field of Search ................................. 568/854, 853, 568/852, 868

(56) References Cited

U.S. PATENT DOCUMENTS 5,345,004 A * 9/1994 Nishiguchi .................. 568/865

FOREIGN PATENT DOCUMENTS

| JP | 63156738 A | * | 6/1988 |
| JP | 07258129 A | * | 10/1995 |

* cited by examiner

*Primary Examiner*—Johann Richter
*Assistant Examiner*—Elvis O. Price
(74) *Attorney, Agent, or Firm*—Morgan & Finnegan, L.L.P.

(57) ABSTRACT

High purity 1,3-butylene glycol obtained from acetaldol by a liquid phase hydrogen reduction method, by adding a base to crude 1,3-butylene glycol free of high-boiling material, heat-treating the mixture and then distilling off 1,3-butylene glycol; and distilling off low-boiling materials from 1,3-butylene glycol. In high performance liquid chromatography analysis under specified conditions, each peak eluted in a relative retention time range of 4.0 to 5.5, taking a relative retention time of 1,3-butylene as 1.0, has an absorbance of 0.02 or less at a measuring wavelength of 210 nm. This has no odor and shows less change with time.

8 Claims, 2 Drawing Sheets

1,3 BUTYLENE GLYCOL OF HIGH PURITY AND METHOD FOR PRODUCING THE SAME

This is the National Phase Application of PCT/JP99/04275, filed Aug. 6, 1999.

BACKGROUND OF THE INVENTION

1. Field of the Invention

The present invention relates to high purity 1,3-butylene glycol and to production method thereof. More particularly, it relates to high purity 1,3-butylene glycol which a small content of impurities eluted for a specified relative retention time range in HPLC (high performance liquid chromatography) analysis under specified conditions and hence is free of odors and has less change with time and to a method for producing high purity 1,3-butylene glycol by adding a base to crude 1,3-butylene glycol or low quality product, heat treating and distilling.

2. Description of Related Art 1,3-Butylene glycol is a viscous, colorless and transparent, odorless liquid that has a boiling point of 208° C. and shows excellent solubility and produces derivatives having excellent chemical stability.

It finds use as a raw material for various synthetic resins, surfactants and also is used as a material for cosmetics, hygroscopic agents, high-boiling solvents, anti-freezes, etc., making the best of its excellent hygroscopicity, low volatility, and low toxicity. In particular, recently, needs for non-toxic, non-irritating 1,3-butylene glycol have been increasing in the field of cosmetics industry since it has excellent properties as a humectant, and odorless butylene glycol is useful as a cosmetic grade.

However, 1,3-butylene glycol obtained by the conventional methods causes changes with time during storage in a tank to generate a slight odor so that it is difficult to store it for a long time.

Therefore, it has been desired to provide 1, 3-butylene glycol free of slight odor after a long-term storage.

JP-A-7-258129 discloses as a method for increasing the yield of odorless product, a method in which at least one compound selected from sodium hydroxide, potassium hydroxide, sodium hydrogen borohydride and potassium borohydride upon distillation for removing high-boiling materials. However, the odorless 1,3-butylene glycol obtained by this method has the problem that it still generates a slight odor due to changes with time after a long-term storage.

SUMMARY OF THE INVENTION

Therefore, an object of the present invention is to provide high purity 1,3-butylene glycol having no odor and showing less changes with time and a production method therefor.

The present inventors have made intensive study with view to solving the problem described in JP-A-7-258129 and as a result it has been found that when distillation is performed by adding an alkali metal to a charge stock solution into a de-high-boiling distillation tower, the charge stock solution in the de-high-boiling distillation tower contains a large amount of high-boiling materials and hence the added alkali metal base causes reaction decreasing low-boiling materials and simultaneously generation of low-boiling materials due to decomposition reaction of high-boiling materials. As a result, odor-causing materials can be decreased only to a certain level so that after a long-term storage there occurs a change with time to generate a slight odor.

Accordingly, the present inventors have made further investigation and have found that in a process for distilling and purifying 1,3-butylene glycol, odor-causing materials can be effectively decreased by adding an alkali metal base to crude 1,3-butylene glycol from which high-boiling materials have been removed in advance, heat-treating, distilling off 1,3-butylene glycol to separate the alkali metal base and high-boiling materials as residues, and then distilling off a low-boiling material form the 1,3-butylene glycol fraction. The present invention has been accomplished based on this finding.

Further, the present inventors have found that in HPLC (high performance liquid chromatography) analysis, 1,3-butylene glycol having an absorbance at a specified wavelength of a peak eluted in a specified relative retention time range is odorless and shows less change with time, thus accomplishing the present invention.

That is, the present invention provides the following:

(1) 1,3-Butylene glycol wherein in high performance liquid chromatography analysis under specified conditions, each peak eluted in a relative retention time range of 4.0 to 5.5, taking a relative retention time of 1,3-butylene as 1.0, has an absorbance of 0.02 or less at a measuring wavelength of 210 nm.

(2) 1,3-Butylene glycol as described in (1) above, wherein the 1,3-butylene glycol is produced from acetaldol by a liquid phase hydrogen reduction method.

(3) A method for producing 1,3-butylene glycol, comprising the steps of: adding a base to crude 1,3-butylene glycol free of high-boiling material, heat-treating the mixture and then distilling off 1,3-butylene glycol; and distilling off low-boiling materials from 1,3-butylene glycol.

(4) The method for producing 1,3-butylene glycol as described in (3) above, wherein the 1,3-butylene glycol is produced from acetaldol by a liquid phase hydrogen reduction method.

(5) The method for producing 1,3-butylene glycol as described in (4) above, wherein the crude 1,3-butylene glycol free of high-boiling material is obtained from reaction product obtained from acetaldol by a liquid phase hydrogen reduction method and is distilled from a de-high-boiling material distillation tower after removal of alcohols, of water, and of salts and high-boiling materials.

(6) The method for producing 1,3-butylene glycol as described (3), wherein the base is sodium hydroxide, potassium hydroxide, or a mixture thereof.

DETAILED DESCRIPTION OF THE INVENTION

Figure 1:
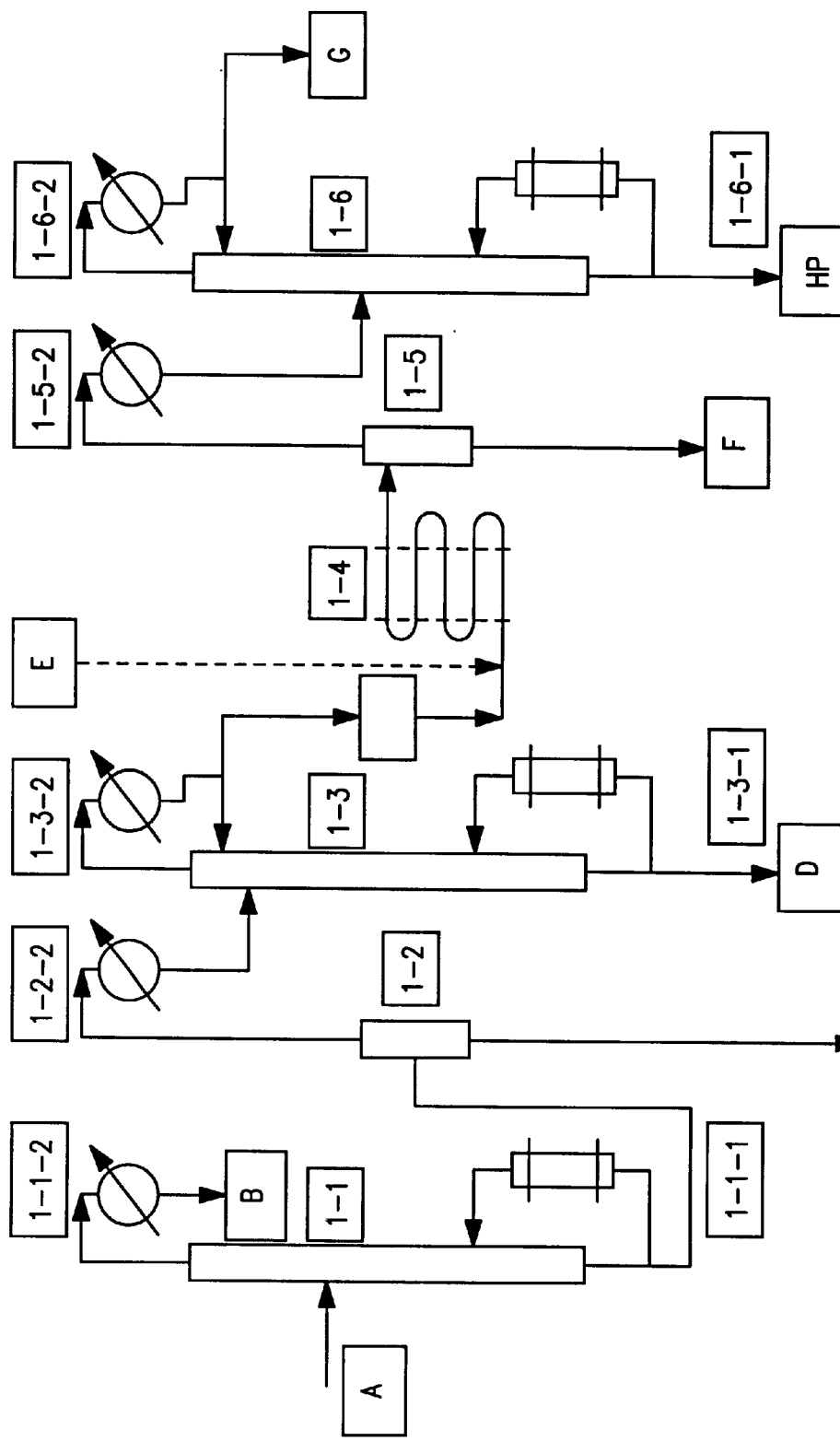
FIG. 1 is an example of flow sheet for practicing a method for producing 1,3-butylene glycol according to the present invention.

Hereinafter, embodiments of the present invention will be explained. 1,3-Butylene glycol according to the present invention is preferably one produced from acetaldol by a liquid phase hydrogen reduction method. However, it may be one produced from 1,3-butylene oxide by a hydrolysis method or mixtures of these or any 1,3-glycol may be used.

In the liquid phase hydrogen reduction method for acetaldol, low-boiling compounds having unsaturated bonds such as acetaldehyde, butyraldehyde, crotonaldehyde, acetone, methyl vinyl ketone, etc., which are considered to be odor-causing materials, or condensates of these are by-produced. These are difficult to remove completely even by distillation. Therefore, in the conventional purification methods, minute amounts of such odor-causing materials tend to mix in the resulting 1,3-butylene glycol. The above odor-causing material means those that are source of odor themselves or become odor materials by changes with time.

The conventional purification method is a method in which the reaction mixture of 1,3-butylene glycol produced by liquid phase hydrogen reduction of acetaldol is subjected to removal of alcohols, removal of water, removal of salts and high-boiling materials and removal of high-boiling materials, then in the low-boiling material removal distillation tower (product distillation tower) low-boiling materials are distilled off from the top of the tower and 1,3-butylene glycol is obtained as a product from the tower bottom.

The present invention has the feature that addition of a base to crude 1,3-butylene glycol having a low content of high-boiling materials and heat-treating the mixture effectively decreases odor-causing materials and gives rise to 1, 3-butylene glycol having no odor and shows less change with time.

In the present invention, the crude 1,3-butylene glycol fed to the purification step is crude 1,3-butylene glycol of which high-boiling materials have been removed, for example, crude 1,3-butylene glycol (CR) after the de-high-boiling material distillation described later on, 1,3-butylene glycol obtained from the product distillation tower in the above-mentioned conventional purification process, low quality product 1,3-butylene glycol, product 1,3-butylene glycol of unknown origin, or mixtures of these and preferably crude ,3-butylene glycol (CR) after the de-high-boiling material distillation.

Crude 1,3-butylene glycol as just obtained by hydrogenation of acetaldol has a high-boiling material content of usually 3 to 7%. In contrast, the crude 1,3-butylene glycol after the removal of high-boiling materials according to the invention has a high-boiling materials content of 1.0%by weight or less, preferably 0.5% by weight or less.

Use of crude 1,3-butylene glycol having a low high-boiling material content generates no or minimized amounts of low-boiling materials due to decomposition reaction of high-boiling materials when heat-treated together with a base, so that the low-boiling materials causing odor can be preferentially decreased due to the reaction with alkali.

As a result, since the absolute amounts of low-boiling materials can be decreased infinitely close to 0, it is possible to produce 1,3-butylene glycol of very high quality, having no odor and showing less change with time.

The low-boiling materials causing odor are considered to be those having unsaturated bonds such as aldehydes and ketones and hence it is considered that addition of a base to crude 1,3-butylene glycol and heat-treating converts impurities to high-boiling materials or causes them to be subject to reduction with hydrogen (hereafter, simply referred to reduction) to form alcohols, so that the absolute amount of impurities is decreased.

FIG. 1 is a flow sheet for an apparatus for use in an embodiment obtaining high purity 1,3-butylene glycol of the present invention, illustrating the situation of charging a base from the portion indicate in broken line.

Reference numeral 1-1 designates a dehydration tower, 1-2 designates a desalting tower (thin film evaporator), 1-3 designates a de-high-boiling material distillation tower, 1-4 designates an alkali reactor, 1-5 designates a dealkalization tower (thin film evaporator), 1-6 designates a product distilling tower. 1-1-1, 1-3-1, and 1-6-1 designate reboilers, respectively, and 1-1-2, 1-2-2, 1-3-2, 1-5-2, and 1-6-2 designate condensers, respectively.

A stands for crude 1, 3-butylene glycol liquid after the liquid phase hydrogen reduction treatment of acetaldol and dealcoholation, B stands for discharged water, C stands for salt and high-boiling materials, D stands for high-boiling materials, CR stands for crude 1,3-butylene glycol after the de-high-boiling material distillation, E stands for a base, F stands for a base and high-boiling material, G stands for a low-boiling material, HP stands for high purity 1,3-butylene glycol.

Crude 1,3-butylene glycol distilled by the de-high-boiling material distillation tower 1-3 is fed to the alkali reactor (for example, a circulating tube type reactor) 1-4. At the same time, a base is added in an amount of 0.05 to 10% by weight, preferably 0.1 to 1.0% by weight, based on the crude 1,3-butylele glycol (CR). If the addition amount of the base is above 10% by weight, the base precipitates in the distillation tower, piping, etc. to cause clogging thereof while the addition amount is too large, contrariwise, decomposition reaction of high-boiling compounds occurs to generate odor-causing materials. On the contrary, with less than 0.05% by weight, the effect to the odor-causing material is less. Thus, the both are undesirable. 1,3-butylene glycol is fed to the alkali reactor 1-4.

In the method for producing 1,3-butylene glycol according to the present invention, the base to be added is preferably an alkali metal compound, more preferably sodium hydroxide, potassium hydroxide, sodium (bi)carbonate, most preferably sodium hydroxide, potassium hydroxide or mixtures thereof. The base may be added in the form of solids as it is, but it is preferred to add as an aqueous solution for ease of operation and for promoting contact with the target solution.

Suitable reaction temperature in the alkali reactor 1-4 is 90 to 140° C., preferably 110 to 130° C. This is because, if the reaction temperature is lower, a longer reaction retention time is necessary, which requires a larger volume reactor and is uneconomical. If the reaction temperature is too high, the odor of 1,3-butylene glycol increases. The reaction retention time is 5 to 120 minutes, preferably 10 to 30 minutes. If the retention time is shorter, the reaction is insufficient, thus deteriorating the quality of final product. If the retention time is longer, a larger reactor is necessary, which increases appliance costs and is disadvantageous economically.

The crude 1,3-butylene glycol to be charged in the alkali reactor may be any crude 1, 3-butylene glycol so far as high-boiling materials have been removed therefrom as described above. For example, it may be those distilled off from high-boiling material distillation tower or those product 1,3-butylene glycol obtained from the tower bottom of the product distillation tower of the above conventional method.

After discharged from the alkali reactor, the crude reaction mixture is treated in the step where 1,3-butylene glycol is distilled off to give the base and high-boiling materials as residues and the step where low-boiling materials are distilled off from 1,3-butylene glycol.

Preferably, the crude reaction mixture is fed first to the dealkalization tower 1-5 (thin film evaporator) where the base used in the reaction and the resulting high-boiling materials are removed from the tower bottom. The evaporator used as a dealkalization tower is a natural flow-down type thin film evaporator and forced stirring type thin film evaporator whose retention time is short are suitable for suppressing thermal hysteresis to the process fluid.

In the evaporator, evaporation is carried out at a reduced pressure of 100 torr or less, preferably 5 to 20 torr, at the top of the tower. For the odor of 1,3-butylene glycol, it is preferred to lower distillation (evaporation) temperature and the lower the pressure is, the more suitable. Conducting distillation under the above conditions maintains the temperature of evaporator to 90 to 120° C. From the top of the tower, 1,3-butylene glycol containing low-boiling materials is distilled off and is charged to the next product distillation tower.

The product distillation tower may be a porous plate tower, a foamed bell tower, etc. Preferably, it is a filled tower having a low pressure loss, filled with Sulzer Packing, Melapack (both are trade names for products by Sumitomo Heavy Industries, Ltd.), etc. is more suitable. This is because 1,3-butylene glycol is thermally decomposed at 200° C. or higher to affect adversely on odor (JP-A-63-156738) so that distillation temperature is to be lowered as low as possible. When thermal hysteresis (retention time) to 1,3-butylene glycol is long, similarly influenced. Therefore, the reboiler to be adopted is suitably a thin film evaporator, such as a natural flow-down type thin film evaporator or a forced stirring type thin film evaporator.

The product distillation may depend on the concentration of low-boiling material in the charge stock solution, but when the concentration of low-boiling material in the charge stock solution is 5% or less, it may be one having a theoretical number of daylights of about 10 to 20 (trays). It is preferred that the charge stock solution is fed at a position from the top of the tower to a height 20 to 70% of the height of the tower. At this time, distillation is performed under reduced pressure of 100 torr or less, preferably 5 to 20 torr, at the top of the tower. For the odor of 1,3-butylene glycol, it is preferred to lower distillation temperature. The lower the pressure is, the more suitable. It is desirable to run distillation at a reflux ratio of 0.5 to 2.0.

The charging into the product distillation tower is carried out by feeding the liquid obtained by concentrating the top of the tower vapor of the dealkalization tower in the condenser 1-5-2. Of course, to decrease the calorie for heating the product distillation tower, the top of the tower vapor from the dealkalization tower may be directly fed to the production tower. 1,3-Butylene glycol product can be obtained from the tower bottom of the product distillation tower.

In the present invention, 1, 3-butylene glycol may be obtained also as follows. That is, the treated liquid from the alkali reactor is fed first to the low-boiling material removal distillation tower where low-boiling materials are distilled off, subsequently 1,3-butlene glycol extracted from the gas phase portion in the recover trays or from the tower bottom is distilled or evaporated to remove the base and the resulting high-boiling materials as distillation residues and 1,3-butylene glycol is recovered from the top of the tower or in the midway of concentration trays.

The distillate of the above low-boiling materials may further be fed to an additional distillation tower where 1 ,3-butylene glycol is distilled off to remove high-boiling materials. Also, a portion of the 1,3-butylene glycol after removal of the above low-boiling materials may be recycled to the dealkalization tower. Alternatively, low-boiling materials containing 1,3-butylene glycol may be recycled to the alkali reactor.

Figure 2A:
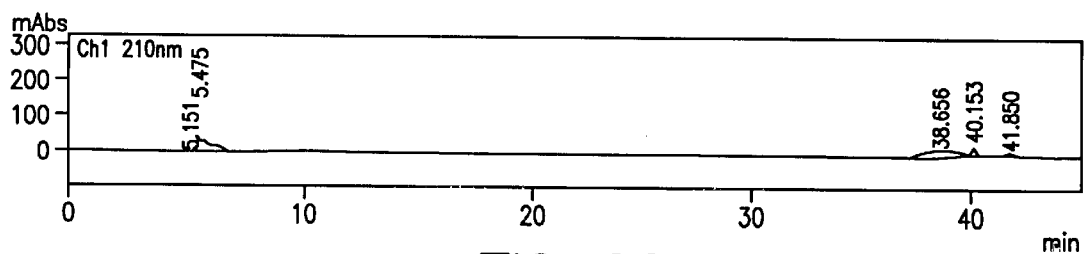
FIG. 2 is a chart of HPLC analysis of 1,3-butylene glycol relative to Examples and Comparative Examples, with FIGS. 2A, 2B, and 2C relating to Example 1, Example 2, and Comparative Example 1, respectively.
Figure 2B:
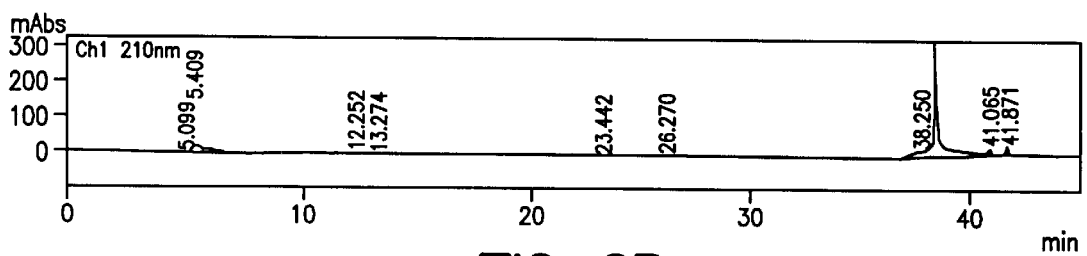
Figure 2C:
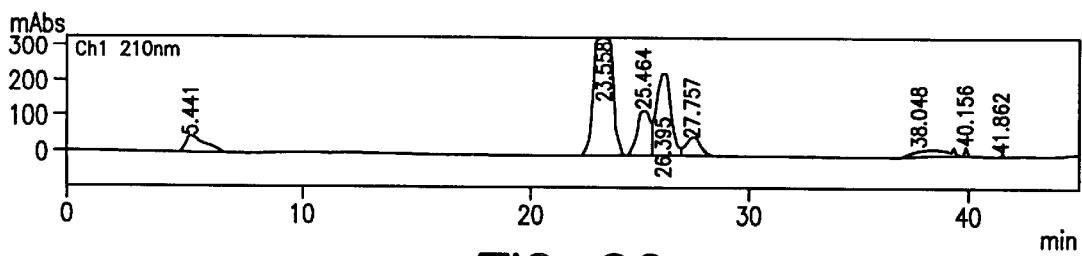

FIG. 2 is a chart of HPLC analysis (measurement wavelength: 210 nm) of 1,3-butylene glycol under specified conditions (which will be described in detail in the column of examples). FIG. 2A is a chart which illustrates the product of Example 1, FIG. 2B is a chart which illustrates the product of Example 2, and FIG. 2C is a chart which illustrates the product of Comparative Example 1. The horizontal axis represents elution time (where a peak exists, its retention time is indicated in minute), the vertical axis represents milli abosorbance (mAbs).

1,3-Butylene glycol has substantially no absorbance in ultraviolet regions, the peak is very small and its retention time is near 5.5 minutes in FIG. 2A, near 5.4 minutes in FIG. 2B, and near 5.4 minutes in FIG. 2C.

The impurities treated in the present invention have retention time of 20 to 30 minutes and products of low grades have large peaks appear near 23.5 minutes, 25.4 minutes, 26.4 minutes, 27.7 minutes, as shown in FIG. 2C, that is, they have high absorbances. On the other hand, in the case products are of relatively good quality, only small peaks (absorbance 0.005 or less) will appear near 23.4 minutes and 26.3 minutes as shown in FIG. 2B. In the case products are of very high quality, no peak will appear in the range of 20 to 30 minutes (absorbance 0.005 or less).

Also, it reveals that the peak near 38 to 42 minutes gives substantially no influence on the odor and change with time.

That is, it reveals that various peaks eluted in a relative retention time in the range of 4.0 to 5.5 taking the relative retention time of 1,3-butylene glycol as 1.0, have an absorbance at 210 nm of 0.02 or less, preferably 0.01 or less, the problems of odor and change with time can be solved.

The high purity 1,3-butylene glycol obtained by the above production method in the above HPLC analysis showed an absorbance at 210 nm of 0.02 or less for each peak eluted in a relative retention time in the range of 4.0 to 5.5, having no odor and less change with time.

EXAMPLES

Hereafter, the present invention will be explained concretely in more detail. However, the present invention is not limited thereto.

All "parts" used in examples and comparative examples are by weight unless otherwise indicated specifically.

Evaluation of 1,3-butylene glycol was made as follows.
1. Odor evaluation:

As evaluation samples, 1,3-Butylene glycol of which no odor was felt was assigned 1, 1,3-butylene glycol substantially odorless was assigned 5, and 1,3-butylene glycol of which slight odor was felt was assigned 10, and scores were obtained by relative evaluation. The evaluation samples were each mixed with water in a ratio of 1:1, and charged in a jar with a ground-in stopper. This was sealed and left to stand at room temperature. Then the odor was smelled quickly in the air, and compared and scored.
2. Test on change with time:

The sample charged in a jar with a ground-in stopper, the gas portion was nitrogen-sealed. Thereafter, the sealed sample was stored in an incubator kept at 40° C. for 3 months and then subjected to HPLC analysis and odor evaluation.
3. Ultraviolet spectroscopic (UV) analysis:

Analyzer: Shimadzu Spectrophotometer UV-12000

Cell width (light path length): 10 mm

Solution in reference cell: Distilled water

Sample: A solution of product 1,3-butylene glycol diluted in distilled water to 10 vol%

Measurement: Absorbance at a measuring wavelength of 210 nm was measured.

4. HPLC analysis:

Analyzer: Shimadzu LC6A

Detector: SPD-M10A (light path length of cell 10 m)

Detection wavelength: 210 nm Analysis column: ODS column YMCpackA-312 ($\phi$: 4.6 mm×120 mm) two columns Analysis condition: Column temperature 40° C.

Moving phase: Acetonitrile/0.2% $H_3PO_4$ aqueous solution=20/80 (vol ratio)

Flow rate of moving phase: 1.2 ml/min.

Sample injection amount: 25 $\mu$l of 10 w/v % 1,3-butylene glycol moving phase solution Absorbance at a measuring wavelength of 210 nm of each peak eluted in a relative retention time in the range of 4.0 to 5.5 taking the relative retention time of 1,3-butylene glycol as 1.0 was measured.

EXAMPLE 1

A method of the present invention is explained based on examples in accordance with a flow sheet shown in FIG. 1. 100 parts of acetaldol and 6.5 parts of hydrogen were charged into a liquid phase hydrogen reduction reactor (not shown) as materials. Then, Raney nickel was added thereto as a catalyst, and the reactor was maintained at a temperature of 125 to 135° C. and a pressure of 150 kg/cm$^2$, and liquid phase hydrogen reduction was conducted. After the reaction, the catalyst was removed from the liquid and the liquid was neutralized with sodium hydroxide. Removal of alcohols therefrom afforded crude 1,3-butylene glycol (A).

The crude 1,3-butylene glycol (A) was charged into dehydration tower 1-1 shown in FIG. 1. In the dehydration tower, water was released from the top of the tower, and 15 parts of fresh water per 100 parts of charged liquid volume was added as a reflux to obtain crude 1,3-butylene glycol containing 0.5% by weight or less of water at a pressure of 50 torr from the bottom of a distillation tower.

Then, dehydrated crude 1,3-butylene glycol was charged into ademineralization tower 1-2. Here, 5 parts per 100 parts of charged liquid volume of a part of salts, high-boiling point materials, and the 1,3-butylene glycol were discharged from the bottom. 95 parts per 100 parts of charged liquid volume of a part of the 1,3-butylene glycol and low/high boiling point materials were distillated.

A part of the 1,3-butylene glycol and low/high boiling point materials, which were distillated from the demineralization tower 1-2, were charged into a high-boiling point materials removal distillation tower 1-3, 20 parts of a part of high boiling point materials and the 1,3-butylene glycol were discharged from the bottom. 80 parts of the crude 1,3-butylene glycol (CR) containing low boiling materials was distilled from the top of the tower and the glycol was charged into an alkali reactor 1-4. In this time, 10% by weight of sodium hydroxide solution was added so as to be 0.2% by weight of sodium hydroxide to the charged liquid. The reaction was conducted for a retention time of 20 and the temperature in the alkali reactor was maintained at 120° C.

A crude reaction liquid, which flew out of the reactor, was charged into a dealkalization tower. In this case, 10 parts per 100 parts of the charged liquid of a part of sodium hydroxide, high-boiling point materials, and 1,3-butylene glycol were discharged. 90 parts per 100 parts of the charged liquid of 1,3-butylene glycol and low boiling point materials were distilled from the top of the tower, and charged into the next production tower. In a production distillation tower 1-6, 10% by weight per 100 parts of a charged liquid of a part of low boiling materials and 1,3-butylene glycol were distilled from the top of the tower, product 1,3-butylene glycol was extracted from the bottom of the tower.

1,3-butylene glycol of immediately after production had 3 of odor marks and 0.001 of an absorbance at 210 nm by an ultraviolet spectrophotometer under the prescribed conditions. And the glycol had 0.005 or less of the absorbance of each peak which eluted in the range of 4.0 to 5.5 for relative retention time in the HPLC analysis.

A test for change with time using this 1,3-butylene glycol was conducted at 40° C. The odor marks was 3 and the absorbance at 210 nm by an ultraviolet spectrophotometer under the prescribed conditions was 0.001 after 1 month. According to this result, no change was observed.

3 Month later, the absorbance at 210 nm by an ultraviolet spectrophotometer under the prescribed conditions was 0.002 which was little increased, and the amount of minute impurities was increased to some extent. However, the absorbance of each peak which eluted in the range of 4.0 to 5.5 for relative retention time in the HPLC analysis was 0.005 or less, and the odor marks was 3 and still odorless. The result was shown in Table 1.

EXAMPLE 2

1,3-Butylene glycol was produced in the same manner as the reaction in Example 1 except that the reaction was conducted at a temperature of 100° C. and a retention time of 30 minutes.

Comparative Example 1

The process was run in the same manner as in Example 1 up to the step of the high-boiling materials removal distillation tower 1-3. 1,3-Butylene glycol and low boiling point materials were distillated from the top of the high-boiling materials removal distillation tower 1-3. The distillated liquid was charged into the production tower as it is. In the production tower 1-6, 10% by weight per 100 parts of the charged liquid of a part of low boiling materials and 1,3-butylene glycol were distillated from the top of the tower. Product 1,3-butylene glycol was extracted from the bottom of the tower.

1,3-Butylene glycol of immediately after production had 3 of odor marks and 1.131 of an absorbance at 210 nm by an ultraviolet spectrophotometer under the prescribed conditions. The glycol had 0.005 or more of the absorbance of each peak which eluted in the range of 4.0 to 5.5 for relative retention time in the HPLC analysis.

A test for change with time using this 1,3-butylene glycol was conducted at 40° C. The odor marks was 5 and the absorbance at 210 nm by an ultraviolet spectrophotometer under the prescribed conditions was 1.160 after 1 month. According to this result, no change was observed. 3 Month later, the odor marks was 10 and the absorbance at 210 nm by an ultraviolet spectrophotometer under the prescribed conditions was 1.193. The absorbance of each peak which elute in range of 4.0 to 5.5 for related retaining time in the HPLC analysis was 0.005 or more and a small quantity of odor was occurred. The result was shown in Table 1.

Comparative Example 2

Sodium hydroxide was added when conducting distillation of high-boiling materials in accordance with the method described in JP-A No. 7-258129. The process was run in the same manner as in Example 1 up to the step of the demineralization tower 1-2. A part of 1,3-butylene glycol and low/high boiling point materials which were distillated from the top of the demineralization tower 1-2 were charged into the distillation of high-boiling point materials tower 1-3. In this time, 10% by weight of sodium hydroxide solution was added so as to be 0.5% by weight of sodium hydroxide to the charged liquid. In the high-boiling materials removal distillation tower, 20 parts of high boiling materials, sodium hydroxide, and 1,3-butylene glycol was discharged from the bottom. 80 parts of the 1, 3-butylene glycol containing low boiling materials was discharged from the top of the tower and the glycol was charged into a next production tower.

In the production tower 1-6, 10% by weight per 100 parts of the charged liquid of a part of low boiling point materials and 1,3-butylene glycol were distillated from the top of the tower and product 1,3-butylene glycol was extracted from the bottom of the tower.

1,3-Butylene glycol of immediately after production had 3 of odor marks and 0.793 of an absorbance at 210 nm by an ultraviolet spectrophotometer under the prescribed conditions. And some glycol had 0.05 or more of the absorbance of each peak which eluted in the range of 4.0 to 5.5 for relative retention time in the HPLC analysis.

A test for change with time using this 1,3-butylene glycol was conducted at 40° C. The odor marks was 4 and the absorbance at 210 nm by an ultraviolet spectrophotometer under prescribed conditionwas 0.847 after 1 month. And 3 month later, the odor marks was 7 and the absorbance at 210 nm by an ultraviolet spectrophotometer under prescribed condition was 0.928. Some absorbance of peak which eluted in range of 4.0 to 5.5 for relative retention time in the HPLC analysis was 0.05 or more and a slight odor occurred.

boiling solvent, an anti-freeze, in particular toiletry materials making the best of hygroscopicity, low-volatility, and low-toxicity.

What is claimed is:

1. 1,3-Butylene glycol wherein in high performance liquid chromatography analysis under specified conditions, each peak eluted in a relative retention time range of 4.0 to 5.5, taking a relative retention time of 1,3-butylene as 1.0, has an absorbance of 0.02 or less at a measuring wavelength of 210 nm.

2. 1,3-Butylene glycol as claimed in claim 1, wherein the 1,3-butylene glycol is produced from acetaldol by a liquid phase hydrogen reduction method.

3. A method for producing 1,3-butylene glycol, comprising the steps of:
   adding a base to crude 1,3-butylene glycol free of high-boiling material, heat-treating the mixture and then distilling off 1,3-butylene glycol; and
   distilling off low-boiling materials from 1,3-butylene glycol.

4. The method for producing 1,3-butylene glycol as claimed in claim 3, wherein the 1, 3-butylene glycol is produced from acetaldol by a liquid phase hydrogen reduction method.

5. The method for producing 1,3-butylene glycol as claimed in claim 4, wherein the crude 1,3-butylene glycol free of high-boiling material is obtained from reaction product obtained from acetaldol by a liquid phase hydrogen reduction method and is distilled from a de-high-boiling material distillation tower after removal of alcohols, of water, and of salts and high-boiling materials.

6. The method for producing 1,3-butylene glycol as claimed in claim 3, wherein the base is sodium hydroxide, potassium hydroxide, or a mixture thereof.

7. 1,3-Butylene glycol having a UV absorbance of less than 0.793 at 210 nm when analyzed at any time up to three months after production.

TABLE 1

| | Odor | | | UV absorbance | | | HPLC absorbance | |
|---|---|---|---|---|---|---|---|---|
| | Just after | After 1 month | After 3 month | Just after | After 1 month | After 3 month | Just after | After 3 month |
| Example 1 | 3 | 3 | 3 | 0.001 | 0.001 | 0.002 | 0.005 or less | 0.005 or less |
| Example 2 | 3 | — | 3 | — | — | — | 0.01 or less | 0.01 or less |
| Comparative Example 1 | 3 | 5 | 10 | 1.131 | 1.160 | 1.193 | 0.05 or more | 0.05 or more |
| Comparative Example 2 | 3 | 4 | 7 | 0.793 | 0.847 | 0.928 | 0.05 or more | 0.05 or more |

According to the present invention, a high quality of 1,3-butylene glycol, which is non-odor and little changing with time is provided. And the glycol can be used for a synthetic resin, a surfactant, a hygroscopic agent, a high- 8. The 1,3-butylene glycol according to claim 7, wherein the UV absorbance is less than or equal to 0.002 at 210 nm.

* * * * *